United States Patent
Mantri et al.

(10) Patent No.: US 12,329,582 B2
(45) Date of Patent: Jun. 17, 2025

(54) APPARATUS TO DETECT TISSUE STRETCHING DURING INSERTION OF PROBES

(71) Applicant: PROCEPT BioRobotics Corporation, Redwood City, CA (US)

(72) Inventors: Surag Mantri, East Palo Alto, CA (US); Kevin Patrick Staid, Lowell, MA (US); Peter Bentley, Reno, NV (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 74 days.

(21) Appl. No.: 17/816,339

(22) Filed: Jul. 29, 2022

(65) Prior Publication Data

US 2023/0255599 A1    Aug. 17, 2023

Related U.S. Application Data

(60) Provisional application No. 63/268,184, filed on Feb. 17, 2022.

(51) Int. Cl.
| | |
|---|---|
| *A61B 8/08* | (2006.01) |
| *A61B 8/00* | (2006.01) |
| *A61B 8/12* | (2006.01) |

(52) U.S. Cl.
CPC ............. *A61B 8/485* (2013.01); *A61B 8/12* (2013.01); *A61B 8/5223* (2013.01)

(58) Field of Classification Search
CPC .......... A61B 8/485; A61B 8/12; A61B 8/5223
See application file for complete search history.

(56) References Cited

U.S. PATENT DOCUMENTS

| | | |
|---|---|---|
| 3,971,364 A | 7/1976 | Fletcher |
| 8,840,571 B2 | 9/2014 | Egorov |
| (Continued) | | |

FOREIGN PATENT DOCUMENTS

| | | |
|---|---|---|
| CN | 113633372 | 11/2021 |
| CN | 113796952 | 12/2021 |
| (Continued) | | |

OTHER PUBLICATIONS

International Search Report and Written Opinion for PCT/US2023/062701, 14 pages (Jul. 20, 2023).

(Continued)

*Primary Examiner* — Amal Aly Farag
(74) *Attorney, Agent, or Firm* — FisherBroyles, LLP; John K. Shimmick

(57) ABSTRACT

Systems, methods, and apparatuses detect tissue strain associated with tissue resistance and shearing and provide feedback such as real time feedback during insertion of a probe, which can decrease potential tissue damage associated with insertion of a probe. In some embodiments, a method may include generating one or more digital images of a tissue, determining a strain imparted on the tissue based on the one or more digital images, and providing feedback based on the detected strain. The feedback may be one or more of audible, visual, or haptic feedback. The feedback may be provided when the determined strain is above a threshold. The strain may be determined through the use of an artificial intelligence or machine learning classifier.

12 Claims, 8 Drawing Sheets

(56) References Cited

U.S. PATENT DOCUMENTS

| | | | |
|---|---|---|---|
| 2006/0058592 A1 | 3/2006 | Bouma | |
| 2011/0105898 A1 | 5/2011 | Guthart | |
| 2011/0264038 A1 | 10/2011 | Fujimoto | |
| 2012/0041295 A1 | 2/2012 | Schultz | |
| 2012/0265069 A1 | 10/2012 | Sliwa | |
| 2014/0276233 A1 | 9/2014 | Murphy | |
| 2014/0354792 A1* | 12/2014 | Poquet | A61B 10/0241 348/77 |
| 2015/0366546 A1* | 12/2015 | Kamen | A61B 5/055 600/461 |
| 2016/0374652 A1 | 12/2016 | Nygaard | |
| 2017/0035991 A1 | 2/2017 | Rankin | |
| 2017/0215802 A1 | 8/2017 | Byron | |
| 2019/0247132 A1 | 8/2019 | Harks | |
| 2020/0037983 A1* | 2/2020 | Poland | A61B 8/14 |
| 2020/0261178 A1 | 8/2020 | Murdeshwar | |
| 2021/0121251 A1 | 4/2021 | Aljuri | |
| 2021/0401521 A1 | 12/2021 | Mantri | |
| 2024/0285346 A1 | 8/2024 | Shi | |
| 2024/0299003 A1 | 9/2024 | Shi | |

FOREIGN PATENT DOCUMENTS

| | | |
|---|---|---|
| CN | 113940753 | 1/2022 |
| CN | 113951935 | 1/2022 |
| CN | 114145781 | 3/2022 |
| CN | 216675776 | 6/2022 |
| CN | 216675785 | 6/2022 |
| CN | 217338655 | 9/2022 |
| JP | H06154154 | 6/1994 |
| WO | 2008083407 | 7/2008 |
| WO | 2009111736 | 9/2009 |
| WO | 2011097505 | 8/2011 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |
| WO | 2016037137 | 3/2016 |
| WO | 2017161331 | 9/2017 |
| WO | 2019032986 | 2/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |
| WO | 2021096741 | 5/2021 |
| WO | 2021130229 | 7/2021 |
| WO | 2021262565 | 12/2021 |
| WO | 2021263276 | 12/2021 |
| WO | 2022011177 | 1/2022 |
| WO | 2022226103 | 10/2022 |
| WO | 2023066148 | 4/2023 |
| WO | 2023072146 | 5/2023 |
| WO | 2023083352 | 5/2023 |
| WO | 2023088305 | 5/2023 |
| WO | 2023159096 | 8/2023 |
| WO | 2023159101 | 8/2023 |

OTHER PUBLICATIONS

As-filed International Patent Application No. PCT/US2022/025617, 117 pages (Apr. 20, 2022).

* cited by examiner

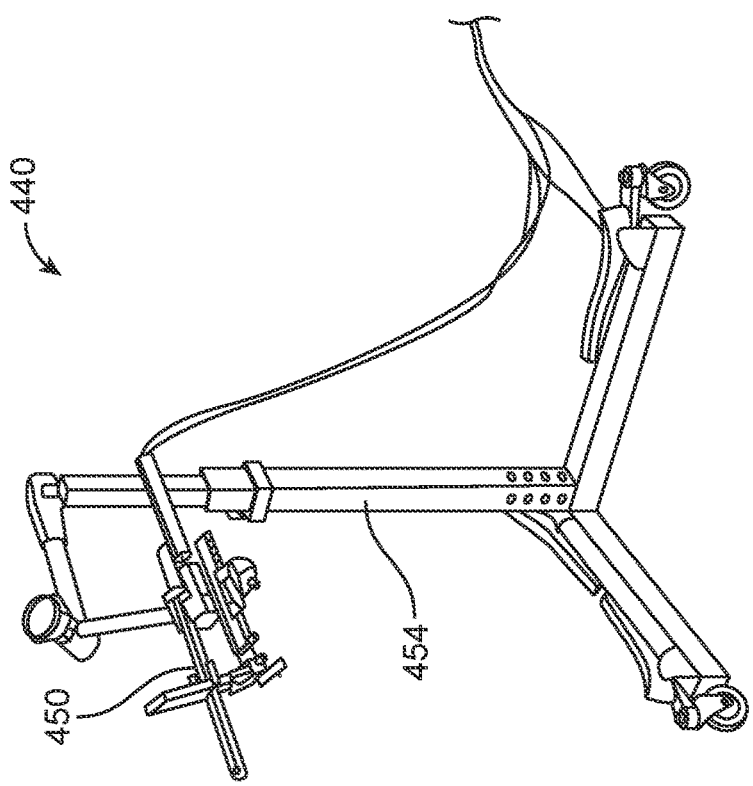
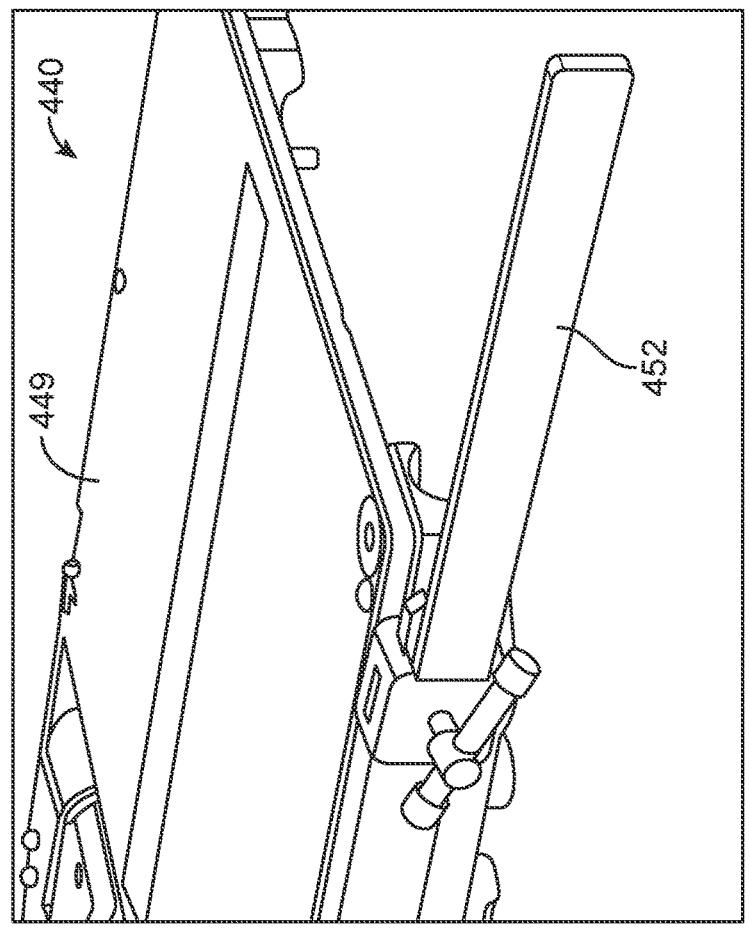
FIG 3A
FIG 3B

APPARATUS TO DETECT TISSUE STRETCHING DURING INSERTION OF PROBES

RELATED APPLICATIONS

The present application claims priority to U.S. Provisional Pat. App. 63/268,184, filed Feb. 17, 2022, entitled "SYSTEMS AND METHODS TO DETECT TISSUE STRETCHING DURING INSERTION PROBES", the entire disclosure of which is incorporated herein by reference.

The subject matter of the present application is related to PCT/US2015/048695, filed on Sep. 4, 2015, entitled "PHYSICIAN CONTROLLED TISSUE RESECTION INTEGRATED WITH TREATMENT MAPPING OF TARGET ORGAN IMAGES", published as WO 2016/037137, on Mar. 10, 2016; PCT/US2020/021756, filed on Mar. 9, 2020, entitled "ROBOTIC ARMS AND METHODS FOR TISSUE RESECTION AND IMAGING", published as WO/2020/181290 on Sep. 10, 2020; PCT/US2020/021708, filed on Mar. 9, 2020, entitled "STIFF SHEATH FOR IMAGING PROBE", published as WO/2020/181280 on Sep. 10, 2020; PCT/US2020/058884, filed on Nov. 4, 2020, entitled "SURGICAL PROBES FOR TISSUE RESECTION WITH ROBOTIC ARMS", published as WO/2021/096741 on May 20, 2021; and PCT/US2021/038175, filed on Jun. 21, 2021, entitled "SYSTEMS AND METHODS FOR DEFINING AND MODIFYING RANGE OF MOTION OF PROBE USED IN PATIENT TREATMENT", published as WO/2021/262565 on Dec. 30, 2021; the entire disclosures of which are incorporated herein by reference.

BACKGROUND

Surgical probes are used in many types of surgical procedures. At least some surgical procedures rely on the insertion of a probe into a naturally occurring lumen or body cavity. Work in relation to the present disclosure suggests that there can be a risk of unintended perforation with at least some surgical procedures, in which a natural tissue wall is unintentionally perforated with a probe, such as surgical probe or an imaging probe. For example, transrectal ultrasound (TRUS) can be used to image tissue during surgery such as prostate surgery. While extremely helpful for imaging tissue during surgery, there is a potential risk that a probe such as a transrectal ultrasound may perforate the wall of the rectum or colon in at least some instances. At least some natural lumens may comprise a pockets along the lumen, which may undesirably limit movement of the probe along the lumen, and work in relation to the present disclosure suggests that it may be helpful to detect tissue resistance prior to perforating the tissue.

In light of the above, there is a need for improved systems, apparatuses, and methods for detecting tissue resistance related to insertion of a probe that would ameliorate at least some of the aforementioned limitations of the prior approaches.

SUMMARY

In some embodiments, the presently disclosed systems, methods and apparatuses detect tissue strain associated with tissue resistance and shearing and provide feedback such as real time feedback during insertion of a probe, which can decrease potential tissue damage associated with insertion of a probe. In some embodiments, a method includes generating one or more digital images of a tissue, determining a strain imparted on the tissue based on the one or more digital images, and providing feedback based on the detected strain. The feedback may be one or more of audible, visual, or haptic feedback. The feedback may be provided when the determined strain is above a threshold. The strain may be determined through the use of an artificial intelligence or machine learning classifier.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIGS. 3A and 3B show perspective views of a common base or mount for supporting one or more robotic arms, in accordance with some embodiments;

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for use with many probes and diagnostic and surgical procedures. Although reference is made to a probe comprising a transrectal ultrasound probe inserted transrectally into a colon, the present disclosure is well suited for use with many types of probe inserted into many types of tissues, cavities and lumens, such as vascular lumens, nasal lumens and cavities, urethral lumens, gastric lumens, airways, esophageal lumens, trans esophageal, intestinal lumens, anal lumens, vaginal lumens, trans abdominal, abdominal cavities, kidney surgery, ureter surgery, kidney stones, prostate surgery, tumor surgery, cancer surgery, brain surgery, heart surgery, eye surgery, liver surgery, gall bladder surgery, bladder surgery, spinal surgery, orthopedic surgery arthroscopic surgery, liposuction, colonoscopy, intubation, minimally invasive incisions, minimally invasive surgery, and others The presently disclosed systems and methods are well suited for combination with prior probes such as imaging probes, treatment probes, stiff sheaths, and other probes that can be inserted into a patient. Examples of such probes include laser treatment probes, water jet probes, RF treatment probes, microwave treatment probes, radiation therapy probes, ultrasound treatment probes, high intensity ultrasound treatment probes, phaco emulsification probes, imaging probes, endoscopic probes, resectoscope probes, ultrasound imaging probes, A-scan ultrasound probes, B-scan ultrasound probes, Doppler ultrasound probes, transrectal ultrasound probes, sagittal plane ultrasound imaging probes, transverse plane ultrasound imaging probes, and transverse and sagittal plane ultrasound imaging probes, for example.

The presently disclosed systems and methods are well suited for use with tissue comprising folds in a tissue wall, such as intestinal tissue, vaginal tissue, nasal tissue, and conjunctival tissue. The presently disclosed systems and methods are well suited for protecting tissues from tearing, abrasion and perforation from forces related to insertion of the probe, which in some instances can be related to the probe engaging a fold of tissue.

Figure 1:
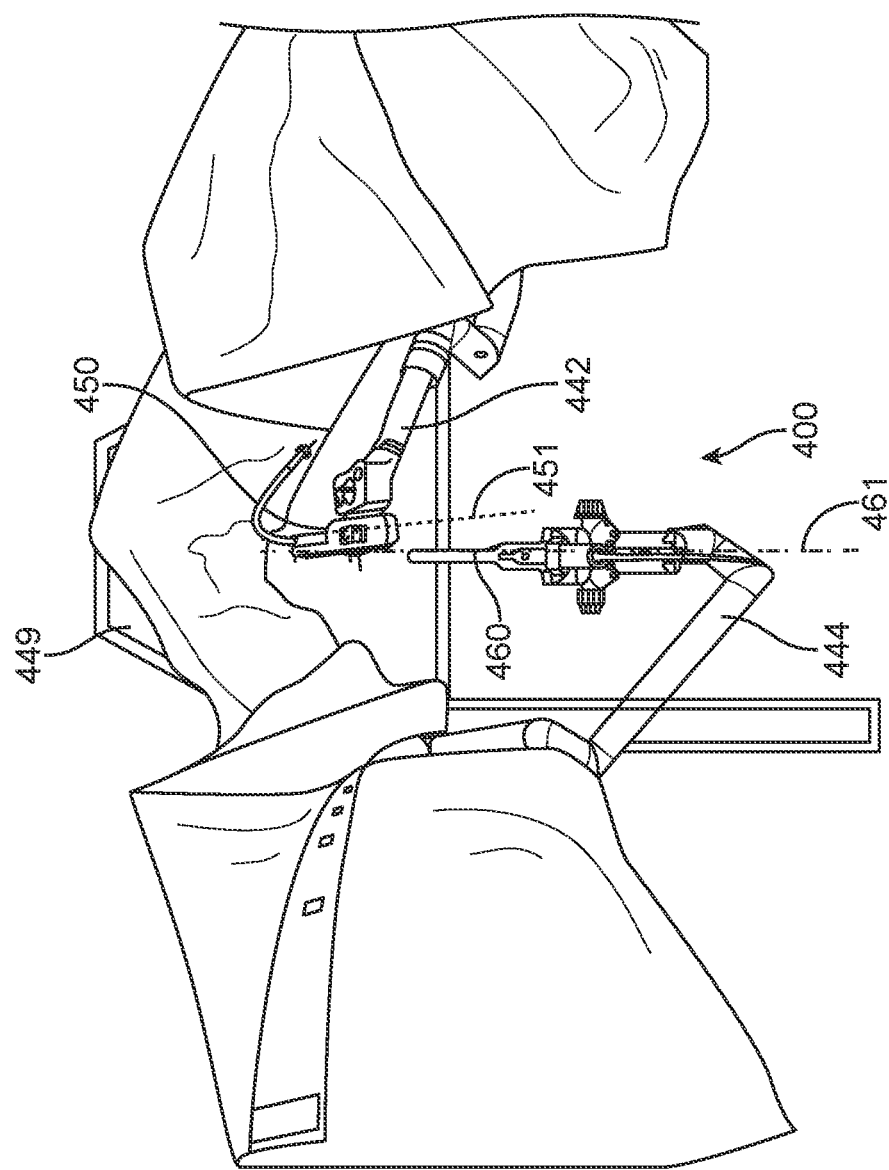
FIG. 1 shows a front view of a system for performing tissue resection in a patient, in accordance with some embodiments.

FIG. 1 shows an exemplary embodiment of a system 400 for performing tissue resection in a patient. The system 400 may comprise a treatment probe 450 and an imaging probe 460. The treatment probe 450 may be coupled to a first arm 442, and the imaging probe 460 coupled to a second am 444. One or both of the first arm 442 and the second arm 444 may comprise robotic arms, also referred to herein as instrument device manipulators, whose movements may be controlled by one or more computing devices operably coupled with the arms. The treatment probe 450 may comprise a device for performing any suitable diagnostic or treatment procedure, and may include resecting, collecting, ablating, cauterizing, or a combination of these or other treatments to tissue from a target site within a patient. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms.

Figure 2:
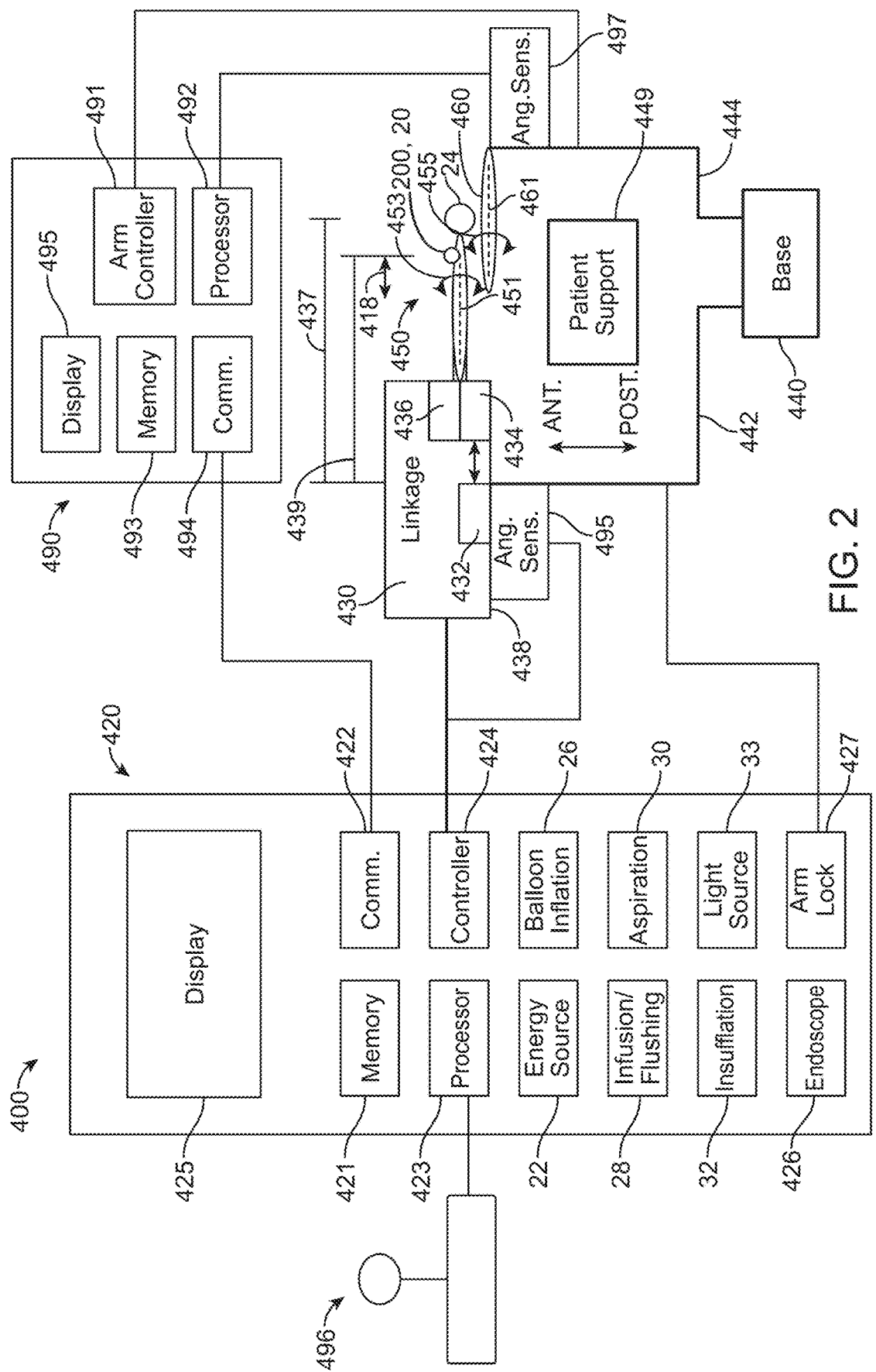
FIG. 2 schematically illustrates a system for performing tissue resection in a patient, in accordance with some embodiments.

FIG. 2 schematically illustrates an exemplary embodiment of the system 400 for performing tissue resection in a patient. The system 400 comprises a treatment probe 450 and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated, such as about rotation 453, 455, and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image data of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. The probe 450 may comprise a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed to the substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the high-pressure nozzle 200 in the energy delivery region 20 at a desired axial position along an elongate axis 451 of treatment probe 450.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust in manner 418 in response to computer control to set a target location along the elongate axis 451 of the treatment probe referenced to anchor 24. The first portion of the linkage remains fixed, while the second portion 434 adjusts the position of the energy delivery region 20 along the axis 451. The third portion of the linkage 436 adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, each of the treatment probe and the imaging probe may be coupled to a robotic, computer-controllable arm. For example, referring to system 400 shown in FIG. 2, one or both of the first arm 442 coupled to the treatment probe 450 and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

Either or both robotic arms may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

FIGS. 3A and 3B show exemplary embodiments of a common base or mount 440 for supporting one or more robotic arms of an image-guided treatment system as disclosed herein. FIG. 3A shows a patient support 449 comprising one or more rails 452. The patient support 449 may comprise a surgical table or a platform. One or more robotic arms associated with one or more of the treatment probe or the imaging probe may be mounted to the rails 452, such that the rails function as the common base 440. FIG. 3B shows a common base 440 comprising a floor stand 454 configured to couple to the first robotic arm connected to the treatment probe and/or the second robotic arm connected to the imaging probe. The floor-stand 454 may be positioned between the patient's legs during the treatment procedure.

Figure 4A:
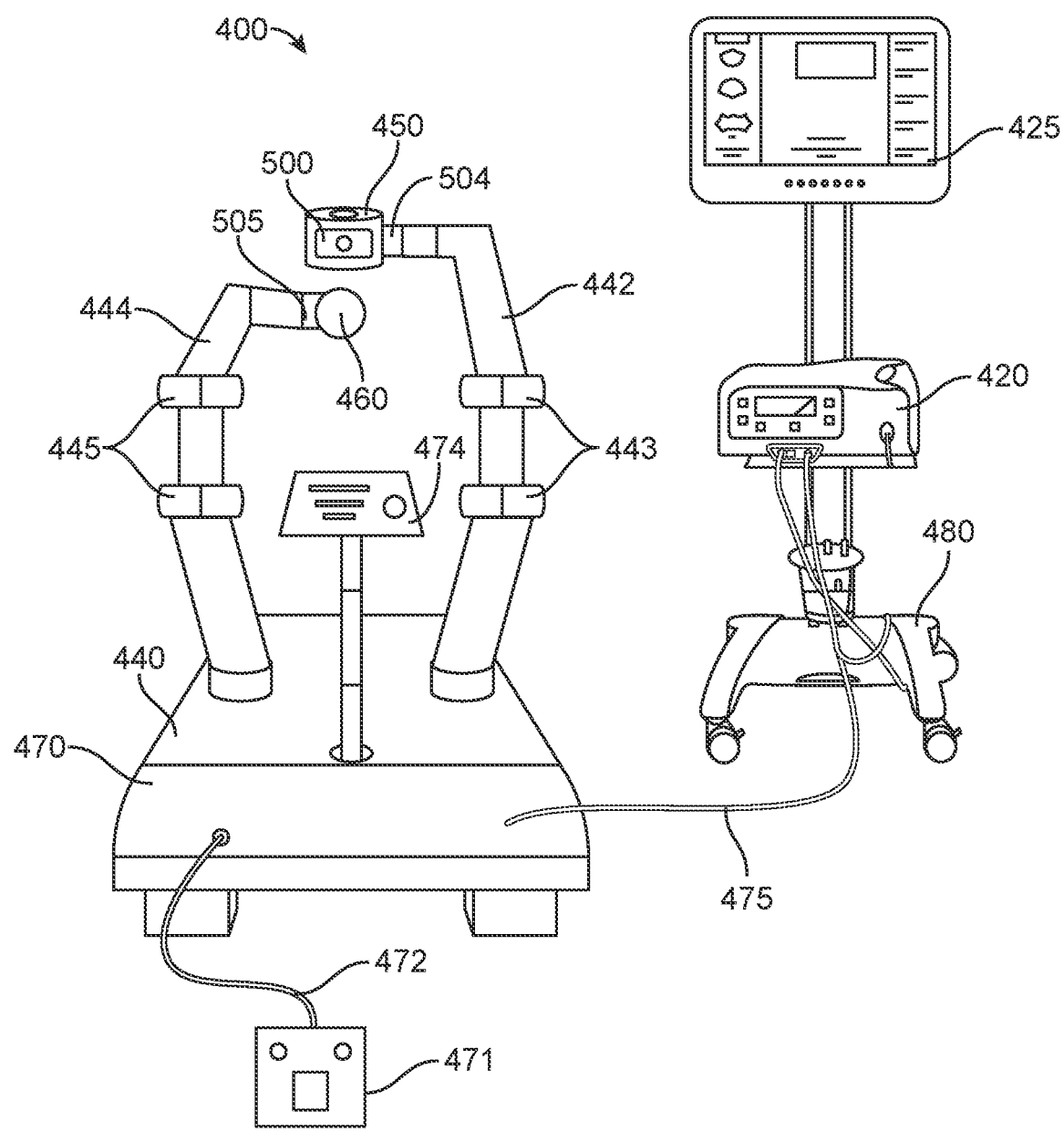
FIGS. 4A and 4B illustrate a perspective and side view, respectively, of a system for performing tissue resection in a patient that comprises a mobile base, in accordance with some embodiments.
Figure 4B:
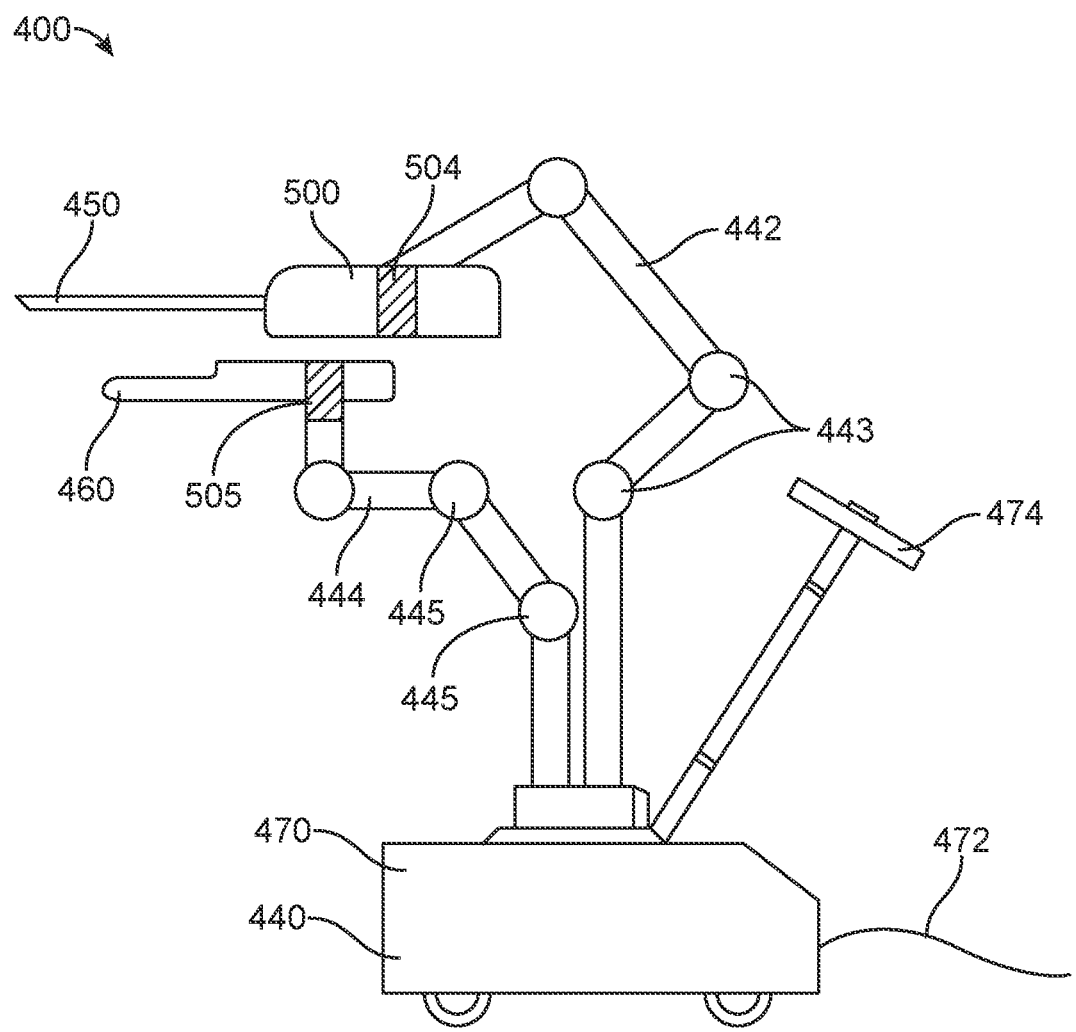

FIGS. 4A and 4B illustrate an exemplary embodiment of a treatment system 400 as described herein comprising a mobile base 470. FIG. 4A is a front view and FIG. 4B is a side view of the treatment system 400. The treatment system 400 comprises a treatment probe 450 coupled to a first robotic arm 442, and an imaging probe 460 coupled to a second robotic arm 444. The first robotic arm 442 and the second robotic arm 444 each comprises a proximal end and a distal end, the distal end coupled to the treatment probe 450 and the imaging probe 460, respectively, and the proximal end coupled to a common base 440 comprising a mobile base 470. The first robotic arm 442 may comprise a first arm coupling structure 504 to couple to the treatment probe 450, and the second robotic arm 444 may comprise a second arm coupling structure 505 to couple to the imaging probe 460. The treatment probe 450 may be coupled to the distal end of the first robotic arm 442 via an attachment device 500, which may comprise a linkage configured to affect movement of the treatment probe as described herein (e.g., rotation, translation, pitch, etc.). Coupling of the treatment probe 450 to the first robotic arm 442 may be fixed, releasable, or user adjustable. Similarly, coupling of the imaging probe 460 to the second robotic arm 444 may be fixed, releasable, or user adjustable.

The first robotic arm 442 may articulate at one or more first arm joints 443. The imaging arm 444 may articulate at one or more second arm joints 445. Each arm joint 443 or 445 may be operably coupled with a computer-controllable actuator, such as a stepper motor, to affect movement at the joint. Each arm joint 443 or 445 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each arm joint 443 or 445 may comprise a linear, orthogonal, rotational, twisting, or revolving joint, or any combination thereof.

The system 400 may further comprise a console 420 as described herein, which may be supported by a mobile support 480 separate from the mobile base 470. The console 420 may be operably coupled with the mobile base 470 via a power and communication cable 475, to allow control of the treatment probe 450 coupled to the mobile base via the first robotic arm. The treatment console 420 comprises a processor and a memory having stored thereon computer-executable instructions for execution by the processor, to control various modules or functionalities of the treatment console, such as an energy source, infusion/flushing control, aspiration control, and other components as described herein with reference to FIG. 2. The treatment console 420 may further comprise a display 425 in communication with the processor. The display 425 may be configured to display, for example, one or more of: subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that has been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 470 may further comprise one or more computing devices to control operation of the one or more robotic arms. For example, the mobile base may comprise processors and a memory having stored thereon computer executable instructions for execution by the one or more processors. The memory may have stored thereon instructions for operating the one or more robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console 420 or a separate imaging console (such as imaging console 490 shown in FIG. 2), wherein the one or more console processors may be configured to execute instructions for controlling movement of the one or more robotic arms, and may communicate the instructions to the robotic arms via communication circuitry (such as communication circuitry 422 of console 420 or communication circuitry 494 of console 490 shown in FIG. 2). The computer executable instructions for controlling movement of the robotic arms may be pre-programmed and stored on a memory, or may be provided by a user via one or more user inputs before or during treatment of the patient using the treatment system.

The one or more computing devices operably coupled with the first and/or second robotic arms may be configured to control movement of the arms so as to adjust the pitch, yaw, roll, and/or linear position of the treatment probe and/or imaging probe along the target site.

The mobile base 470 may comprise one or more user input devices to enable a user to control movement of the robotic arms under computer instructions. For example, as shown in FIGS. 4A and 4B, the mobile base may comprise a keyboard 474 and/or a footswitch 471, the footswitch operably coupled with the mobile base via a footswitch cable 472. The keyboard 474 and the footswitch 471, independently or in combination, may be configured to control operation of the first robotic arm 442 and/or the second robotic arm 444, for example via articulation of one or both robotic arms at one or more joints. The keyboard and the footswitch may be in communication with the one or more processors configured to control movement of the robotic arms. When a user inputs instructions into the keyboard and/or the footswitch, the user instructions can be received by the one or more processors, converted into electrical signals, and the electrical signals may be transmitted to the one or more computer-controllable actuators operably coupled with the one or more robotic arms. The keyboard and/or the footswitch may control movement of one or both arms towards or away from a treatment position, a position of interest, a predetermined location, or a user-specified location, or any combination thereof.

Optionally, the keyboard 474 and the footswitch 471, independently or in combination, may be configured to control operation of the treatment probe 450 and/or imaging probe 460. For example, the keyboard 474 and/or footswitch 471 may be configured to start, stop, pause, or resume treatment with the treatment probe. The keyboard 474 and/or footswitch 471 may be configured to begin imaging or freeze, save, or display on the display 425 an image or sequence of images previously or currently acquired by the imaging probe.

The mobile base 470 and the mobile support 480 of the console 420 may be independently positionable around a patient, supported by a patient support 449 such as a platform. For example, the mobile base 470, supporting the first and second robotic arms and the treatment and imaging probes, may be positioned between the patient's legs, while the mobile support 480 carrying the console 420 and the display 425 may be positioned to the side of the patient, such as near the torso of the patient. The mobile base 470 or the mobile support 480 may comprise one or more movable elements that enable the base or the support to move, such as a plurality of wheels. The mobile base 470 may be covered with sterile draping throughout the treatment procedure, in order to prevent contamination and fluid ingress.

The probe such as TRUS probe 460 shown in FIGS. 1 to 4B can be advanced into the patient in many ways in accordance with the present disclosure. In some embodiments, the probe is advanced manually. The manual advancement may be provided by the physician pushing on the probe. Alternatively or in combination, the probe is advanced manually by the physician manipulating a proximal control such as a knob coupled to a rack and pinion drive to advance and retract the probe. In some embodiments, the manual drive comprises one or more sensors such as encoders or linear displacement voltage transducers (LVDTs) to measure movement of the probe during insertion and retraction of the probe.

In some embodiments, the one or more sensors is coupled to a processor to receive displacement data such as axial displacement of the probe, and this displacement data is combined with tissue data to detect tissue resistance.

Figure 5:
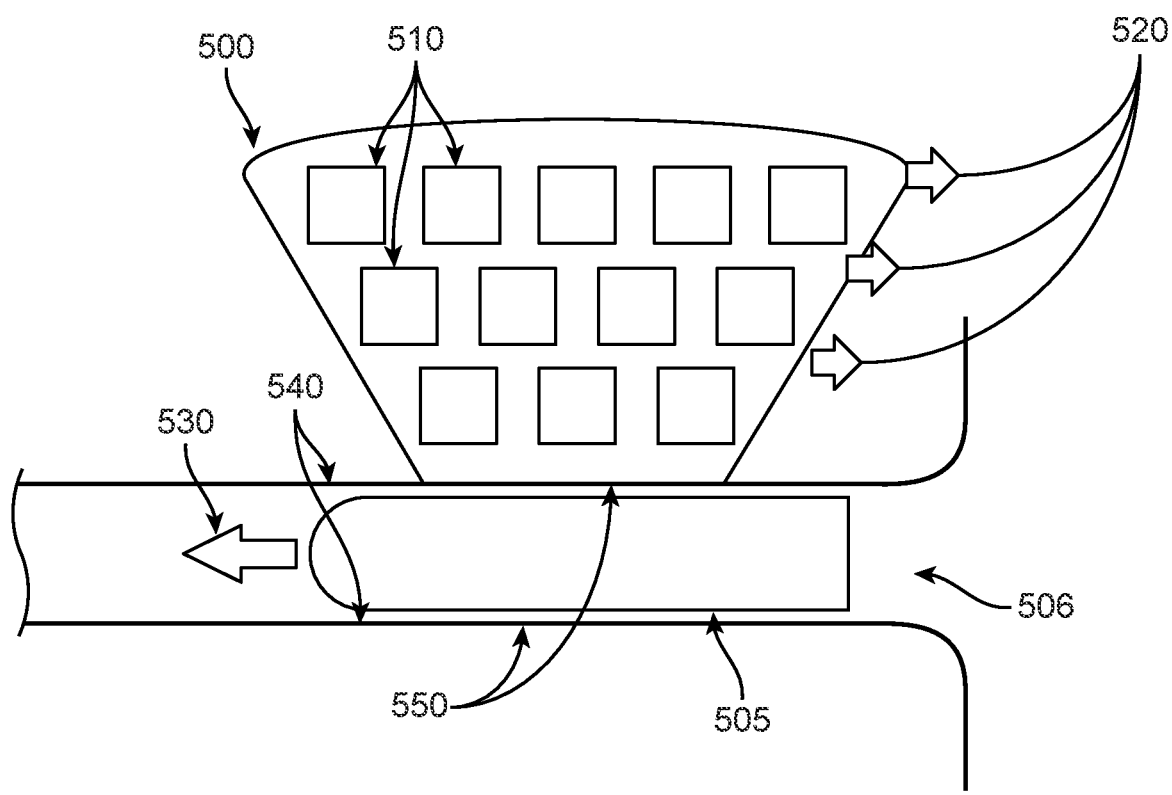
FIG. 5 shows a probe and associated imaging of the surrounding tissue during normal advancement of the probe in tissue, in accordance with some embodiments.

FIG. 5 shows a probe 505 and associated image 500 of the surrounding tissue 550 during normal advancement of the probe in tissue, in accordance with some embodiments herein. The image 500 may be digital or analog images of the surrounding tissue and may be displayed on a screen for observation and monitoring by a medical professional, such as a doctor. In some embodiments, the digital or analog images may not be displayed on the screen and instead may be merely processed and analyzed by a processor without display on the screen. In some embodiments, the image may be displayed on a screen and processed or analysis by a processor. Image 500 may include one or more anatomic structures 510 of the surrounding tissue. The images may depict aspects of the anatomy of a patient. For example, the images may depict the structures of the rectum, intestine, esophagus, trachea, vagina, muscles, fat, colon, prostate, urethra, and other internal tissues of the patient.

The images can be generated with any suitable imager as described herein. The images may be generated via ultrasound imaging. In some embodiments, the images may be generated with intracorporeal ultrasound imaging. For example, using an ultrasound imaging probe such as probe 505. In some embodiments, the images may be generated with extracorporeal ultrasound imaging. In some embodiments, other imaging techniques may be used to image the internal anatomy and tissue structure, such as real-time or near real-time imaging techniques including TRUS probes, endoscopes, cystoscopes, optical images, real-time MRI, real-time CT, and OCT scanning.

The probe 505 may be an imaging probe, such as an ultrasound probe, a transrectal ultrasound probe (TRUS probe), or the like. In some embodiments, the probe 505 may be an operating instrument such as a robotic arm with tools attached, a liposuction device, an intubation tube, a vascular probe, a colonoscopy imaging camera, or other tool. The probe may be inserted into the patient's tissue 550 through an opening 506, such as the anus.

The probe 505 may be advanced in a direction 530 through the lumen. During movement of the probe 505, friction at the interface 540 between the interior side walls of the lumen and the probe 505 may resist the movement of the probe 505. Similarly, misguiding of the probe 505 or catching the probe on a pocket or fold of the tissue during advancement of the probe through the lumen may similarly cause the tissue to resist advancement of the probe. In some embodiments, such resistance, misguidance, or catching of the probe in the tissue 550 may cause the probe to apply large forces to the tissue which may result in damage to the tissues 550, such as fissures or tearing.

The image 500 shown in FIG. 5 depicts normal advancement of the probe 505 through the lumen within tissue 550. During normal advancement, the probe and surrounding tissue are subject to minimal friction or catching. The image 500 depicts the anatomic structures 510 in a normal or non-stress state. The anatomic structures 510 are depicted as squares in FIG. 5 for simplicity. However, during use within real tissue, the anatomic structures 510 would take the shape of the structures and anatomy that is imaged.

The depiction of the anatomic structures 510 in the image 500 are shown in an undistorted state due to the minimal resistance between the probe and the tissue during normal advancement of the probe in direction 530. The relative shearing between the layers of the tissue, as depicted by the arrows 520, show that the tissue is subject to the same little to no shearing forces across the depth of the tissue and as a function of distance from the probe.

In some embodiments, the image 500 may be real-time ultrasound video during advancement of the probe 505. In such an embodiment, arrows 520 may indicate that the layers of tissue are moving at the same relative velocity with respect to the probe.

Figure 6:
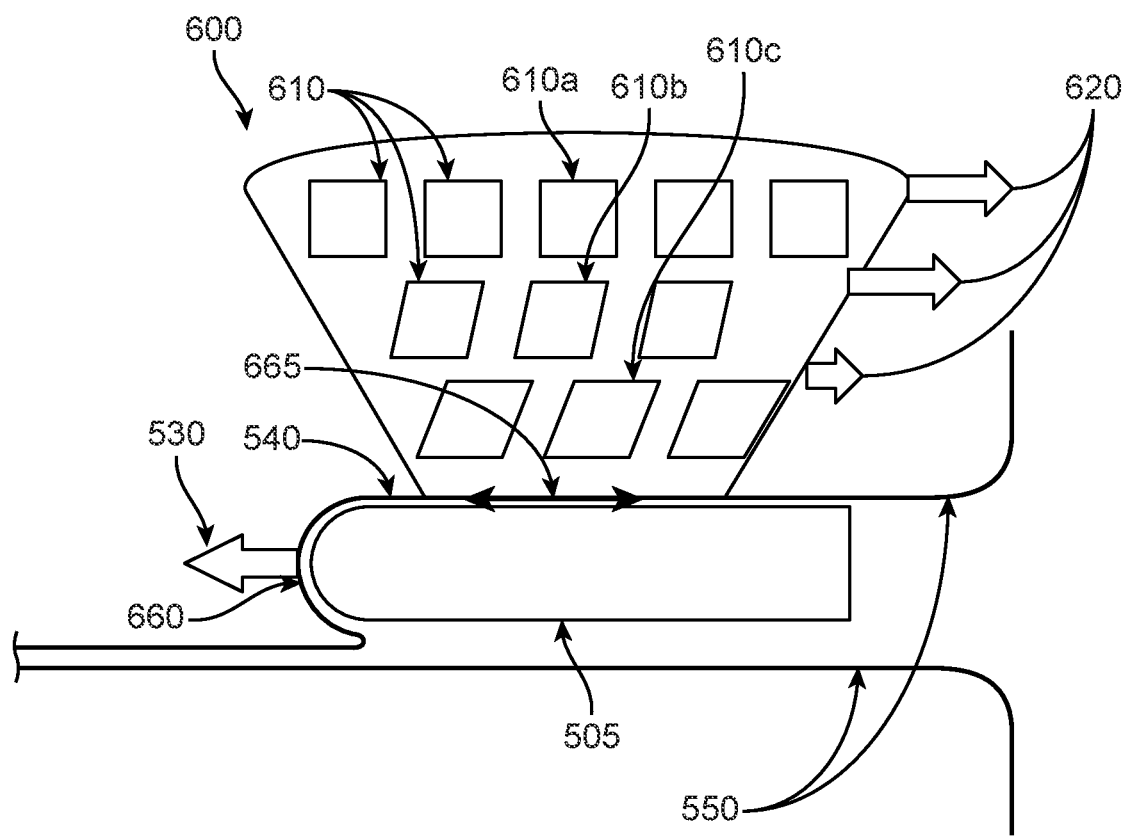
FIG. 6 shows a probe and associated imaging of the surrounding tissue elongation and shearing associated with tissue resistance with advancement of the probe in tissue, in accordance with some embodiments.

FIG. 6 shows the same probe as depicted in FIG. 5 along with the associated imaging of the surrounding tissues. However, the tissue in FIG. 6 is experiencing elongation and shearing associated with the tissue's resistance to the advancement of the probe within the lumen. The image 600 may be digital or analog images of the surrounding the probe 505 and may be displayed on a screen for observation and monitoring by a medical professional, such as a doctor. In some embodiments, the digital or analog images may not be displayed on a screen and instead may be merely processed and analyzed by a processor without display on the screen. Image 600 may include one or more images 610 of the surrounding tissue.

The images may be generated using many medical imaging techniques, for example, using an ultrasound imaging probe, such as probe 505, or other real-time or at least near real-time imaging technique.

The probe 505 may be advanced in a direction 530 through the lumen. During movement of the probe 505, friction at the interface 540 between the interior side walls of the lumen and the probe 505 may resist the movement of the probe 505. Similarly, misguiding of the probe 505 or catching the probe on a pocket or fold of the tissue during advancement of the probe through the lumen may similarly cause the tissue to resist advancement of the probe. In some embodiments, such resistance, misguidance, or catching of the probe in the tissue 550 or at the interface 540 between the tissue and the probe may cause the probe to apply large forces to the tissue which may result in damage to the tissues 550 such as fissures or tearing.

The image 600 shown in FIG. 6 depicts the probe 505 catching the tissue 550 during advancement of the probe 505 through the lumen within tissue 550. This may happen when the tip of the probe catches a pocket 660 or fold formed in the sidewall of the lumen during advancement of the probe into or through the lumen. The image 600 depicts the anatomic structures 610 in a high friction for high strain state wherein a large force being exerted between the probe and the surrounding tissue. That large force is greater than the force exerted on the tissue during normal advancement of the probe. The anatomic structures 610 are depicted as quadrilaterals of varying shapes in FIG. 6 for simplicity in showing the various levels of strain the tissues are being subjected to. However, during use within real tissue, the anatomic structures 610 would take the shape of the structures and anatomy being imaged.

The depiction of the anatomic structures 610 in the image 600 are shown in a distorted state due to the high resistance and forces between the probe and the tissue during abnormal advancement of the probe in direction 530. The relative shearing between the layers of the tissue, as depicted by the arrows 620, show that the tissue is subject to higher shearing than during normal advancement of the probe, such as depicted in FIG. 6.

During abnormal advancement of the probe 505 through the lumen, the tissue immediately surrounding the probe, such as the tissue captured by the probe, may experience relatively high strain and may move with the movement of the probe. The movement of the tissue near the probe with respect to the probe may be less than the movement of tissue further away from the probe, for example as depicted by the differing lengths of the arrow 620. In some embodiments, the image 600 may be real-time ultrasound video during advancement of the probe 505. In such an embodiment, arrows 620 may indicate that the layers of tissue 610a, 610b, 610c are moving at a different relative velocity with respect to the probe. In some embodiments, the location of the tissue features may be tracked over time, such as over multiple images 600 over time. The displacement of the features may be tracked. During treatment, when the probe catches in a pocket or fold of the tissue or experiences high friction with the tissue, the different layers and the tissue features in the layers may be displaced differing amounts. Layers more proximal to the probe, such as layer 610c being displaced more than layers distal to the probe, such as layer 610a.

In some embodiments, the thickness of tissue may be monitored to determine whether or not the tissue subject to high strain. For example, the thickness of a tissue may be monitored over time or in comparison with known or average thicknesses in order to determine that the tissue is subject to high strain. In some embodiments, for example when imaging, the thickness of the wall of the rectum may be monitored. When the probe catches on a pocket or fold within the intestine or the rectum the wall 665 may be stretched, causing localized thinning of the wall 665. A relative change in the thickness of the wall during imaging may indicate high strain. A measured thickness of the wall below a threshold value may also indicate high strain in the wall of the rectum. In some embodiments, the wall 665 or tissue more proximal to the probe, such as layer 610c may be elongated more than distal layers, such as layer 610a as the probe is advanced in the lumen.

In some embodiments, the tissue may elongate as the probe is advanced into the lumen when the tip catches a fold or pocket of the tissue. The elongation may cause different relative movement of the tissue with respect to the probe. For example, tissue closer to the tip or distal end of the probe may experience less movement or displacement relative to the probe than tissue at the proximal end of the probe due to the elongation of the tissue as the probe is advanced in the lumen.

The probe may also detect tissue compressions, such as may occur when the tip of the probe is caught in a fold or pocket of tissue. In such embodiments, the tip may compress the tissue in contact with the tip in near the tip. The amount of compression and/or an amount of force imparted on the tissue may be determined based on the image 600.

In some embodiments, one or more images is analyzed to detect the tissue resistance. For example each of layer 610a, layer 610b, and layer 610c may comprise a resolvable tissue structure that can be identified at a location in the one or more images. The plurality of tissue structures at the plurality of locations in the one or more images can be used to detect the strain based on the plurality of locations, such as with relative movement of the tissue structures as viewed in the one or more images. In some embodiments, the one or more images comprises a first image and a second image, in which the first image comprises the plurality of tissue structures at a first plurality of locations, and the second image comprises the plurality of tissue structures at a second plurality of locations. The strain can be detected in response to differences among the first plurality of locations and the second plurality of locations, for example with reference to shearing 620. In some embodiments, the plurality of tissue structures comprises a first tissue structure at first distance from the probe and a second tissue structure at a second distance from the probe greater than the first distance. The strain can be detected based on the first tissue structure moving less than the second tissue structure between the first image and the second image. For example, with tissue resistance the tissue closer to the probe will move at least partially with the probe whereas tissue farther from the probe will tend to remain at substantially the same physical location, such that tissue closer to the probe moves less in the images than the tissue farther from the probe.

In some embodiments, the probe is coupled to one or more encoders so as to measure movement of the probe, such as with a linkage coupled to the probe as described herein. The movement of the probe can be compared to the movement of one or more tissue structures to detect strain associated with tissue resistance. With decreased tissue resistance associated with decreased strain, the movement of the tissue structure in the image will substantially correspond to movement of the probe, whereas with increased resistance and strain the corresponding movement of the tissue structure in the one or more images will be less than the movement of the probe. The movement may comprise rotational or translational movement, for example.

In some embodiments, the one or more digital images comprises a first image and a second image, in which the first image comprises a tissue structure at a first location, the second image comprises the tissue structure at a second location, and the strain is determined based on the first location and the second location. In some embodiments, the strain is detected based on a movement of probe and a difference between the first location of the tissue structure and the second location of the tissue structure corresponding to less movement than the movement of the probe. In some embodiments, the movement of the probe comprises a distance of axial advancement of the probe into the tissue along an elongate axis of the probe from a first position for the first image to the second position for the second image, and the difference between the first location in the first image and the second location in the second image corresponds to an amount of movement less than the distance of axial advancement. In some embodiments, the movement of the probe comprises a rotation angle around an elongate axis of the probe from a first angle for the first image to a second angle for the second image and the difference between the first location and the second location corresponds to an amount of movement less than the rotation angle. These probe movements may comprise rotational and translational movements performed with a linkage comprising encoders coupled to a processor as described herein.

The locations of the plurality of tissue structures can be determined with any suitable ways as will be appreciated by one of ordinary skill in the art. Non limiting examples include machine learning, artificial intelligence, neural networks, and convolutional neural networks, and other approaches as described herein for example. A processor can be configured to train or teach the appropriate detection algorithm, e.g. a classifier, as described herein.

Real-time imaging of the tissue may be used to observe the distorted tissue or changes in relative movement between tissue near the probe compared to tissue further from the probe or in the thickness of tissues in order to determine that the probe is caught on tissue or otherwise subjecting the tissue to high forces that may potentially result in tearing or other damage to the patient's tissue.

Machine learning or artificial intelligence may be used in order to detect distortions in the image 600. The present disclosure provides several examples methods and system for using surgical robotics data and imaging data with machine learning to train a machine learning algorithm, and any type of patient data and surgical robotics data as described herein can be used. For example, ultrasound parameters such as the gain, frequency, depth, tissue type, probe location, field of view, brightness and contrast, whether imaging at fundamental or harmonic frequencies of the emitter, relative location of emitters for compound imagining, and others can be used. Additional parameters for machine learning may include the treatment planning profiles, such as the radius, angle and longitudinal position of the cut profile, for example when conducting and monitoring tissue ablation when using the probe. These settings and configurations may be combined with real time imaging from the imaging devices such as ultrasound probes, TRUS probes, endoscopes, cystoscopes, and optical images. The images may comprise images of tissue structures such as the rectum, intestines, lower intestines, esophagus, fat, blood vessels, abdominal tissue, urethra, bladder neck, and verumontanum, among other tissues including those discussed elsewhere herein. The images may comprise a portion of the surgical instrument such as a rotating and oscillating probe or other tool or robotic arm tool as described herein. The images can be processed with image segmentation, for example, to determine the location of the tissue structure, and the surgical instrument. The artificial intelligence software instructions can be configured to automatically identify the tissue structures and surgical instruments and determine the relative locations of each. The data can be vectorized and input into the machine learning classifier, for example. The imaged tissue structure may comprise any tissue structure as described herein.

An artificial intelligence processor instructions or a machine learning classifier is trained in response to received data described herein, including settings, configuration, and imaging data. The artificial intelligence processor instructions may comprise one or more of machine learning, search and mathematical optimization, artificial neural networks, statistics, probability, support vector machine learning, clustering of data groups, image classification, image segmentation. The machine learning processor instructions may comprise one or more of decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning or a learning classifier system.

The artificial intelligence processor instructions or the machine learning classifier may receive the settings and configurations along the images in order to determine the relative amount of strain to which the tissue is subjected. In some embodiments, the artificial intelligence processor instructions or the machine learned classifier may be trained based on tagged images of tissue undergoing varying amounts of strain. For example, images may be tagged with low, medium, or high strain tags or may be tagged in other ways such as on a scale of 1 to 5 or 1 to 10, with 1 representing low or normal amounts of strain and increasing numbers representing increasing amounts of strain.

Many different tissues may be imaged using medical imaging in order to determine the strain being applied thereto. Transrectal imaging may be used, wherein the probe is inserted through the anus and into the rectum, as discussed above. Other imaging may include vaginal imaging wherein the tissue surrounding the vagina, such as the vaginal wall, the bladder, the rectum, and other anatomy may be imaged. In some embodiments, the imaging may be transesophageal imaging wherein the tissue surrounding the esophagus may be imaged, such as the esophagus wall itself, the lungs, liver, fat, and other tissue surrounding the esophagus may be imaged. In some embodiments, vascular imaging may be conducted wherein veins, arteries, muscular tissue, skin, fat, and other tissue surrounding the veins may be imaged. In some embodiments, trans abdominal imaging may be conducted wherein any of the tissues within the abdomen may be monitored for shearing and thinning such as the intestines, the bladder, the liver, the lungs, fat, and other tissues. In some embodiments, such as during intubation, the trachea and surrounding tissues including the lungs, fat, and other tissues may be imaged. In some embodiments, such as a colonoscopy, the upper and lower intestines may be imaged, the colonoscopy probe may be imaged, and other tissue surrounding the colon may be imaged.

Figure 7:
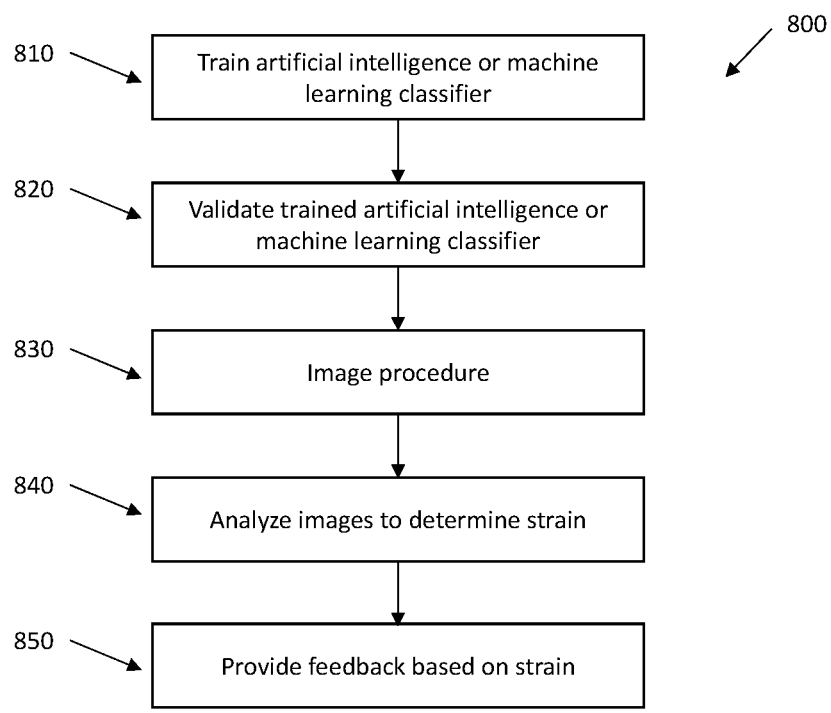
FIG. 7 shows a method of detecting tissue resistance, in accordance with some embodiments.

FIG. 7 shows a method of detecting tissue resistance, in accordance with some embodiments. While the method can be performed in many ways, in some embodiments, an artificial intelligence or machine learning classifier may be trained, the artificial intelligence or machine learning classifier may be validated, the procedure such as a surgery, a colonoscopy, and intubation, or other medical procedure may be imaged, the images may be analyzed, such as by the artificial intelligence or machine learning classifier or other means, to determine a strain on the patient's tissue, and feedback may be provided based on the strain.

At step 810 an artificial intelligence or machine learning classifier is trained. For example, the artificial intelligence or machine learning classifier may be trained using training data. Training data may include images of patient anatomy acquired using imaging processes described herein and tagged with one or more data tags. The data tags may include the amount of strain depicted in the image, the anatomy depicted in the image, the type of medical imaging used to create the image, and other data tags. The training data images from previous procedures have been manually tagged by medical professionals.

While the method can be performed in many ways, in some embodiments, a classifier is trained to recognize anatomical landmarks and features in image data. The method includes comparing anatomical landmarks and features in image data of past patients with the anatomical landmarks and image data as described herein. The anatomical landmarks and features in image data comprise past actual medical imaging of anatomical landmarks and features in image data, among other input types.

Data sets are generated and may be stored in a database comprising historical information, which may comprise a library of actual historical data. The library of patient data can be stored in a database keyed by a unique patient identifier for each patient and associated data for each patient as described herein. The database may comprise a relational database keyed by a unique patient identifier. The historical data stored for each patient may comprise robotics data from the surgery and images from the surgery, for each patient of the database. The database may comprise data from any suitable number of patients, such as at least 100 patients, at least 1000 patients, and at least 10,000 patients, and in some embodiments from 10,000 to 1,000,000 patients. Based upon the data input, as described herein, the method utilizes an appropriate model to generate predicted strain data which is used to train the classifier. The classifier may be validated with the data through iterative training. The validated classifier is then used to receive input from an actual patient and output useful information, such as a proposed resection profile in response to values of targeted safety and efficacy parameters as described herein. The input data may comprise images of past procedures.

A classifier is trained on plurality of anatomical landmarks and features from a plurality of images. This may be performed using one or more image analysis algorithms that allow the classifier such as a convolutional neural network to determine anatomical features displayed with the image data. While the classifier can be trained in many ways, in some embodiments a trained professional such as a radiologist or surgeon identifies landmarks and inputs the locations and type of anatomical landmark with a user interface such as a touchpad. In some embodiments, the trained professional also identifies the relative strain depicted in the image. The anatomical landmarks may comprise one or more delicate tissue structures as described herein, such as a verumontanum, a retina of an eye, or a tumor, for example. This training can be completed for several images from the library of treatments for example.

The training may generate data sets between anatomical structures in their detective shape along with the estimated strain depicted in the image.

At step 820 the trained artificial intelligence or machine learning classifiers are validated. Validation may be an iterative process that compares predicted data regarding estimated strain generated by the artificial intelligence or machine learning classifier against actual data, such as a professional's estimation of the strange shown in the image, and the classifier can be modified until the predicted data converges toward the actual data.

At step 830 the medical procedure is imaged. The medical procedure can be imaged by any of the imaging technologies described herein. In some embodiments, the images may be generated with intracorporeal ultrasound imaging. In some embodiments, the images may be generated with extracorporeal ultrasound imaging. In some embodiments, other imaging techniques may be used to image the internal anatomy and tissue structure, such as real-time or near real-time imaging techniques including, TRUS probes, endoscopes, cystoscopes, optical images, real-time MRI, real-time CT, and OCT scanning. An image or a plurality of images such as a sequential stream of images or a video may be generated by the imaging system during the procedure.

At step 840 the images are analyzed to determine strain on the patient's tissue. One or more of the images may be processed by an artificial intelligence or knowledge machine learning classifier that has been trained as described herein in order to determine much strain the tissue is being subjected to. In some embodiments the strain may be measured qualitatively such as on a scale of 1 to 5 or 1 to 10, or quantitatively based on for example the displacement between tissue near the probe as compared to displacement of tissue.

In some embodiments edge detection or other non-artificial intelligence or machine learning or other image analysis algorithms may be used to track the shape of the tissue features over time during advancement of the probe. By tracking the changing shapes based on the edge detection, an algorithm can determine whether the shapes are changing and by how much and then, based on changes in the shapes, and determine whether or not the tissue is subject to high strain.

At step 850 feedback is provided based on the determined strain. Feedback may be provided to a medical professional in many ways. In some embodiments, feedback may include a gradient alert to a user. In some embodiments, the feedback may be visual feedback. Visual feedback can include a feedback displayed on a screen, for example, a gauge such as a dial gauge, similar to a speedometer needle or tachometer needle. In some embodiments, visual feedback displayed on the screen may include a linear gauge such as a bar chart that changes length based on the amount of detected strain or a bar with an indicator that moves from one end of the bar to another end of the bar with increasing strain. In some embodiments, visual feedback can include color displayed on screen. For example, an icon such as a circle or square changes color from green to yellow to red with increasing strain. In some embodiments, the visual feedback include a colored gauge that also changes color based on the amount of strain. In some embodiments, the visual feedback may include a light emitter such as an LED that changes color based on strain.

In some embodiments, the feedback may be audible feedback. For example no audible feedback may be provided when detected strain is below a first threshold, a first level of audible feedback when strain exceeds a first threshold, and increasing audible feedback as the strain increases or when strain exceeds a second threshold. For example, in some embodiments the first level of audio feedback may be at a first frequency and/or a first volume when the strain exceeds a first threshold, and at a second frequency and second volume when the strain exceeds the second threshold. In some embodiments, the first volume is greater than the second volume. In some embodiments, the first frequency is greater than the second frequency. In some embodiments, the first frequency is less than the second frequency. In some embodiments the audible feedback may occur at intervals such as beeps or tones occurring at increasingly frequent intervals as strain increases. For example, when little to no or normal strain is detected or the strain is below a first threshold the interval between beeps or tones may be 1 Hz or less. In some embodiments, when the strain exceeds a first threshold the interval between beeps or tones may be greater than 1 Hz and increase at increasing strain thresholds or may increase linearly or continually based on the determined strain.

In some embodiments, the gradient alert may be tactile or haptic feedback. In such an embodiment, the tool being operated by the professional, such as a TRUS probe, may vibrate or provide haptic feedback based on the amount of strain measured or determined from the images. For example, when little to no or normal strain is detected when a strain is below a first threshold the tactile or haptic feedback may not be activated. In some embodiments, when the strain exceeds a first threshold the tactile feedback may be provided at a screen frequency and a first magnitude. In some embodiments, when the strain exceeds a second threshold the tactile or haptic feedback may be provided at one or more of a second frequency or a second magnitude. In some embodiments, the tactile or haptic feedback, including the frequency or magnitude or both vary with the strain measured or determined from the images.

In some embodiments, the feedback is binary feedback, wherein the feedback is provided in a first state when the strain is below a threshold and at a second state when the strain is above the threshold. In some embodiments, the feedback may be visual feedback. Visual feedback can include feedback displayed on a screen or changes to a screen. For example, the screen may be on when the strain is below a first threshold and may flash when the strain is above the first threshold. In some embodiments, visual binary feedback can include color displayed on screen. For example, an icon such as a circle or square, or the text or background or both can change from a first color or set of colors when the strain is below a first threshold and to a second color or set of colors on the strain is above the first threshold. In some embodiments, the visual feedback may include a light emitter such as an LED that changes color from a first color to a second color based on the strain increasing above a threshold number.

In some embodiments, the feedback may be audible feedback. For example, the feedback may include providing no audible feedback when detected strain is below a first threshold, audible feedback when strain exceeds the first threshold. In some embodiments, the audible feedback may be an alarm or tone.

In some embodiments, the binary alert may be tactile or haptic feedback. In such an embodiment, the tool being operated by the professional, such as a TRUS probe may vibrate or provide haptic feedback based on the amount of strain measured or determined from the images. For example, when little to no or normal strain is detected or when strain is below a first threshold the tactile or haptic feedback may not be activated. In some embodiments, when the strain exceeds a first threshold the tactile feedback may be provided. at a first frequency and a first magnitude.

The thresholds discussed herein may be set and/or adjusted by a medical professional. The adjustment may occur before or during treatment. For example, a medical professional may receive an alert or feedback regarding the estimated strain or force on the tissue during a procedure, but based on their skill and experience, may determine that the threshold for the alert is too low or too high and may adjust the threshold or thresholds.

One or more steps of the method 800 may be performed with circuitry or processor instructions as described herein, for example, one or more of a processor or a logic circuitry of the systems described herein. The circuitry may be programmed to provide one or more steps of the method 800, and the program may comprise program instructions stored on a computer readable memory or programmed steps of the logic circuitry such as with programmable array logic or a field programmable gate array, for example.

FIG. 7 shows a method in accordance with embodiments. A person of ordinary skill in the art will recognize many variations and adaptations in accordance with the teachings disclosed herein. For example, steps of the method can be removed. Additional steps can be provided. Some of the steps may comprise sub-steps. Some of the steps can be repeated. The order of the steps can be changed.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A method for providing feedback during a procedure, the method comprising: generating one or more digital images of a tissue; determining a strain imparted on the tissue based on the one or more digital images; and providing feedback based on the detected strain.

Clause 2. The method of clause 1, wherein the one or more digital images comprises a first image and a second image, the first image comprising a tissue structure at a first location, the second image comprising the tissue structure at a second location, wherein the strain is determined based on the first location and the second location.

Clause 3. The method of clause 2, wherein the strain is detected based on a movement of a probe and a difference between the first location of the tissue structure and the second location of the tissue structure corresponding to less movement than the movement of the probe.

Clause 4. The method of clause 3, wherein the movement of the probe comprises a distance of axial advancement of the probe into the tissue along an elongate axis of the probe from a first position for the first image to the second position for the second image and the difference between the first location in the first image and the second location in the second image corresponds to an amount of movement less than the distance of axial advancement.

Clause 5. The method of clause 3, wherein the movement of the probe comprises a rotation angle around an elongate axis of the probe from a first angle for the first image to a second angle for the second image and the difference between the first location and the second location corresponds to an amount of movement less than the rotation angle.

Clause 6. The method of clause 1, wherein the tissue structure comprises a plurality of tissue structures at a plurality of locations in the one or more images and the strain is detected based on the plurality of locations.

Clause 7. The method of clause 6, wherein the one or more images comprises a first image and a second image, the first image comprising the plurality of tissue structures at a first plurality of locations, the second image comprising the plurality of tissue structures at a second plurality of locations, wherein the strain is detected in response to differences among the first plurality of locations and the second plurality of locations.

Clause 8. The method of clause 7 wherein the plurality of tissue structures comprises a first tissue structure at first distance from the probe and a second tissue structure at a second distance from the probe greater than the first distance, wherein the strain is detected based on the first tissue structure moving less than the second tissue structure between the first image and the second image.

Clause 9. The method of clause 1, wherein determining a strain includes: analyzing the one or more digital images using an artificial intelligence or machine learning classifier.

Clause 10. The method of clause 9, wherein the artificial intelligence or machine learning classifier has been trained with image data from previous procedures.

Clause 11. The method of clause 10, wherein the data is tagged with a strain.

Clause 12. The method of clause 11, wherein the strain is a qualitative or relative amount of strain.

Clause 13. The method of clause 12, wherein the strain is tagged on a numerical scale.

Clause 14. The method of clause 1, further comprising: training the artificial intelligence or machine learning classifier with image data from previous procedures.

Clause 15. The method of clause 1, wherein imaging includes ultrasound imaging.

Clause 16. The method of clause 15, wherein imaging includes ultrasound imaging with an ultrasound probe.

Clause 17. The method of clause 16, wherein imaging includes ultrasound imaging with a transrectal ultrasound (TRUS) probe.

Clause 18. The method of clause 17, wherein imaging is performed by a probe within the rectum.

Clause 19. The method of clause 1, wherein imaging includes intracorporeal ultrasound imaging.

Clause 20. The method of clause 1, wherein imaging includes extracorporeal ultrasound imaging.

Clause 21. The method of clause 1, wherein imaging includes optical imaging.

Clause 22. The method of clause 1, wherein imaging includes real-time imaging.

Clause 23. The method of clause 1, wherein imaging includes Magnetic Resonance Imaging (MRI), Computed Tomography (CT), or Optical Coherence Tomography OCT imaging.

Clause 24. The method of clause 1, wherein imaging includes imaging with an endoscope or cystoscope.

Clause 25. The method of clause 1, wherein the feedback comprises audible feedback.

Clause 26. The method of clause 25, wherein the audible feedback is an alarm.

Clause 27. The method of clause 26, wherein the alarm is activated when the strain exceeds a threshold.

Clause 28. The method of clause 27, further comprising: comparing the detected strain to a threshold, and wherein providing feedback based on the detected strain includes activating the alarm when the detected strain exceeds the threshold.

Clause 29. The method of clause 25, wherein the audible feedback comprises a tone that varies in one or more of frequency or volume, based on the detected strain.

Clause 30. The method of clause 1, wherein the feedback comprises haptic feedback.

Clause 31. The method of clause 30, wherein the haptic feedback comprises vibration of a tool or a tool handle.

Clause 32. The method of clause 31, wherein the vibration is activated when the strain exceeds a threshold.

Clause 33. The method of clause 31, wherein the vibration varies in one or more of frequency or magnitude, based on the detected strain.

Clause 34. The method of clause 32, further comprising: comparing the detected strain to a threshold, and wherein providing feedback based on the detected strain includes activating the vibration when the detected strain exceeds the threshold.

Clause 35. The method of clause 1, wherein the feedback comprises a visual feedback.

Clause 36. The method of clause 35, wherein the visual feedback comprises color visual feedback.

Clause 37. The method of clause 36, wherein the color visual feedback comprises one or more of activation of a light source, changing a color of the light source, changing a color of an image on a screen, or a flashing the image on the screen.

Clause 38. The method of clause 37, further comprising: comparing the detected strain to a threshold to provide the color visual feedback when the detected strain exceeds the threshold.

Clause 39. The method of clause 35, wherein the visual feedback comprises a depiction of a linear or dial gauge.

Clause 40. An apparatus, the apparatus comprising: a processor configured to perform the method of any one of clauses 1 to 39.

Clause 41. A non-transitory tangible medium configured to perform the method of any one of clauses 1 to 39.

Clause 42. An apparatus comprising: an imager; a processor coupled to an imager, the processor configured for, receiving one or more digital images of a tissue while the probe is inserted into tissue; determining a strain imparted on the tissue based on the one or more digital images; and providing feedback based on the detected strain.

Clause 43. The apparatus of clause 42, wherein the one or more digital images comprises a first image and a second image, the first image comprising a tissue structure at a first location, the second image comprising the tissue structure at a second location, wherein the strain is determined based on the first location and the second location.

Clause 44. The apparatus of clause 43, wherein the strain is detected based on a movement of a probe and a difference between the first location of the tissue structure and the second location of the tissue structure corresponding to less movement than the movement of the probe.

Clause 45. The apparatus of clause 44, wherein the movement of the probe comprises a distance of axial advancement of the probe into the tissue along an elongate axis of the probe from a first position for the first image to the second position for the second image and the difference between the first location in the first image and the second location in the second image corresponds to an amount of movement less than the distance of axial advancement.

Clause 46. The apparatus of clause 44, wherein the movement of the probe comprises a rotation angle around an elongate axis of the probe from a first angle for the first image to a second angle for the second image and the difference between the first location and the second location corresponds to an amount of movement less than the rotation angle.

Clause 47. The apparatus of clause 42, wherein the tissue structure comprises a plurality of tissue structures at a plurality of locations in the one or more images and the strain is detected based on the plurality of locations.

Clause 48. The apparatus of clause 47, wherein the one or more images comprises a first image and a second image, the first image comprising the plurality of tissue structures at a first plurality of locations, the second image comprising the plurality of tissue structures at a second plurality of locations, wherein the strain is detected in response to differences among the first plurality of locations and the second plurality of locations.

Clause 49. The apparatus of clause 48 wherein the plurality of tissue structures comprises a first tissue structure at first distance from the probe and a second tissue structure at a second distance from the probe greater than the first distance, wherein the strain is detected based on the first tissue structure moving less than the second tissue structure between the first image and the second image.

Clause 50. The apparatus of clause 42, wherein determining a strain includes: analyzing the one or more digital images using an artificial intelligence or machine learning classifier.

Clause 51. The apparatus of clause 50, wherein the artificial intelligence or machine learning classifier has been trained with image data from previous procedures.

Clause 52. The apparatus of clause 51, wherein the data is tagged with a strain.

Clause 53. The apparatus of clause 52, wherein the strain is a qualitative or relative amount of strain.

Clause 54. The apparatus of clause 53, wherein the strain is tagged on a numerical scale.

Clause 55. The apparatus of clause 42, further comprising: training the artificial intelligence or machine learning classifier with image data from previous procedures.

Clause 56. The apparatus of clause 42, wherein imaging includes ultrasound imaging.

Clause 57. The apparatus of clause 56, wherein imaging includes ultrasound imaging with an ultrasound probe.

Clause 58. The apparatus of clause 57, wherein imaging includes ultrasound imaging with a transrectal ultrasound (TRUS) probe.

Clause 59. The apparatus of clause 58, wherein imaging is performed by a probe within the rectum.

Clause 60. The apparatus of clause 42, wherein imaging includes intracorporeal ultrasound imaging.

Clause 61. The apparatus of clause 42, wherein imaging includes extracorporeal ultrasound imaging.

Clause 62. The apparatus of clause 42, wherein imaging includes optical imaging.

Clause 63. The apparatus of clause 42, wherein imaging includes real-time imaging.

Clause 64. The apparatus of clause 42, wherein imaging includes Magnetic Resonance Imaging (MRI), Computed Tomography (CT), or Optical Coherence Tomography OCT imaging.

Clause 65. The apparatus of clause 42, wherein imaging includes imaging with an endoscope or cystoscope.

Clause 66. The apparatus of clause 42, wherein the feedback comprises audible feedback.

Clause 67. The apparatus of clause 66, wherein the audible feedback is an alarm.

Clause 68. The apparatus of clause 67, wherein the alarm is activated when the strain exceeds a threshold.

Clause 69. The apparatus of clause 68, further comprising: comparing the detected strain to a threshold, and wherein providing feedback based on the detected strain includes activating the alarm when the detected strain exceeds the threshold.

Clause 70. The apparatus of clause 66, wherein the audible feedback comprises a tone that varies in one or more of frequency or volume, based on the detected strain.

Clause 71. The apparatus of clause 42, wherein the feedback comprises haptic feedback.

Clause 72. The apparatus of clause 71, wherein the haptic feedback comprises vibration of a tool or a tool handle.

Clause 73. The apparatus of clause 72, wherein the vibration is activated when the strain exceeds a threshold.

Clause 74. The apparatus of clause 72, wherein the vibration varies in one or more of frequency or magnitude, based on the detected strain.

Clause 75. The apparatus of clause 72, further comprising: comparing the detected strain to a threshold, and wherein providing feedback based on the detected strain includes activating the vibration when the detected strain exceeds the threshold.

Clause 76. The apparatus of clause 42, wherein the feedback comprises a visual feedback.

Clause 77. The apparatus of clause 76, wherein the visual feedback comprises color visual feedback.

Clause 78. The apparatus of clause 77, wherein the color visual feedback comprises one or more activation of a light source, changing a color of the light source, changing a color of an image on a screen, or a flashing the image on the screen.

Clause 79. The apparatus of clause 78, further comprising: comparing the detected strain to a threshold to provide the color visual feedback when the detected strain exceeds the threshold.

Clause 80. The apparatus of clause 76, wherein the visual feedback comprises a depiction of a linear or dial gauge.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus comprising:
    an ultrasound imaging probe configured to be inserted into a patient;
    a processor configured to be coupled in electronic communication with the ultrasound imaging probe, the processor configured for:
        imaging, with the ultrasound imaging probe, tissue coupled to the ultrasound imaging probe within which the ultrasound imaging probe is located during imaging to generate one or more ultrasound digital images of the tissue with the ultrasound imaging probe at least partially inserted into the tissue, wherein tissue comprises a first tissue structure at a first distance from the ultrasound imaging probe and a second tissue structure at a second distance from the ultrasound imaging probe greater than the first distance;
        detecting a strain imparted on the tissue by the ultrasound imaging probe based on the one or more ultrasound digital images from the ultrasound imaging probe, wherein the strain is detected based on the first tissue structure being displaced less than the second tissue structure between a first ultrasound digital image and a second ultrasound digital image of the one or more ultrasound digital images, wherein a movement of the ultrasound imaging probe comprises a rotation angle around an elongate axis of the ultrasound imaging probe from a first angle for the first ultrasound digital image to a second angle for the second ultrasound digital image and a displacement between the first tissue structure at a first location and the first tissue structure at a second location corresponds to an amount of movement of the tissue between the first ultrasound digital image and the second ultrasound digital image that is less than the rotation angle of the ultrasound imaging probe;
        altering the movement of the ultrasound imaging probe in response to the detected strain.

2. The apparatus of claim 1, wherein a displacement of the ultrasound imaging probe further comprises a distance of axial advancement of the ultrasound imaging probe into the tissue along the elongate axis of the ultrasound imaging probe from a first position for the first image to a second position for the second image and the displacement between the first location in the first image and the second location in the second image corresponds to an amount of displacement of the first tissue structure that is less than the distance of axial advancement of the ultrasound imaging probe.

3. The apparatus of claim 1, wherein detecting the strain includes:
    analyzing the one or more ultrasound digital images using an artificial intelligence or machine learning classifier.

4. The apparatus of claim 3, wherein the artificial intelligence or machine learning classifier has been trained with image data from previous procedures.

5. The apparatus of claim 4, wherein the image data is tagged with a strain.

6. The apparatus of claim 5, wherein the strain is a qualitative or relative amount of strain.

7. The apparatus of claim 6, wherein the strain is tagged on a numerical scale.

8. The apparatus of claim 1, wherein an artificial intelligence or machine learning classifier has been trained with image data from previous procedures.

9. The apparatus of claim 1, wherein the ultrasound imaging probe comprises a transrectal ultrasound (TRUS) probe.

10. The apparatus of claim 9, wherein imaging is performed with the transrectal ultrasound probe within a rectum.

11. The apparatus of claim 1, wherein imaging includes intracorporeal ultrasound imaging.

12. The apparatus of claim 1, wherein imaging includes extracorporeal ultrasound imaging.

* * * * *